United States Patent
Manak, Jr. et al.

(10) Patent No.: US 7,072,444 B1
(45) Date of Patent: Jul. 4, 2006

(54) METHOD AND SYSTEM FOR GENERATING MONOCHROMATIC X-RAYS

(75) Inventors: Joseph John Manak, Jr., Albany, NY (US); John Scott Price, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/094,901

(22) Filed: Mar. 31, 2005

(51) Int. Cl.
*H05G 2/00* (2006.01)

(52) U.S. Cl. ..................... 378/119; 378/121

(58) Field of Classification Search ............. 378/119, 378/121, 137, 138; 250/504 R, 493.1, 494.1, 250/495.1
See application file for complete search history.

(56) References Cited

U.S. PATENT DOCUMENTS

| | | | |
|---|---|---|---|
| 3,886,366 A * | 5/1975 | Kash | 378/119 |
| 6,332,017 B1 | 12/2001 | Carroll et al. | 378/119 |
| 6,687,333 B1 | 2/2004 | Carroll et al. | 378/119 |

* cited by examiner

*Primary Examiner*—Courtney Thomas
(74) *Attorney, Agent, or Firm*—Fletcher Yoder

(57) ABSTRACT

Briefly in accordance with one embodiment, the present technique provides an X-ray source. The X-ray source includes an electron source configured to generate an electron beam. The X-ray source also includes an ultra-violet photon source configured to generate one or more mono-energetic streams of ultra-violet photons. The X-ray source further includes an interaction region configured to facilitate interaction of the electron beam and the one or more mono-energetic streams of ultra-violet photons to generate X-rays having a substantially monochromatic or multimodal distribution.

22 Claims, 3 Drawing Sheets

METHOD AND SYSTEM FOR GENERATING MONOCHROMATIC X-RAYS

BACKGROUND

The invention relates generally to generating X-rays and specifically to a method and system for generating monochromatic X-rays.

X-ray imaging systems are generally utilized for various applications in the medical and non-medical fields. For example, medical X-ray imaging systems, such as radiographic systems, computed tomography (CT) systems, and tomosynthesis systems, are used to create internal images or views of a patient. Based on the attenuation of the X-rays and on the type and amount of data acquired, different views may be constructed, including views showing motion, contrast enhancement, volume reconstructions, two-dimensional images and so forth. Alternatively, X-ray imaging systems may also be utilized to in non-medical applications, such as in industrial quality control or in security screening of passengers, packages, and/or baggage. In such applications, acquired data and/or generated images or volumes may be used to detect objects, shapes or irregularities which are otherwise hidden from casual visual inspection and which are of interest to the screener.

Typically, X-ray imaging systems, both medical and non-medical, utilize X-ray tubes to generate the X-rays used in the imaging process. Often, conventional X-ray tubes emit a broad spectrum of X-rays, i.e., X-rays at a broad range of wavelengths, which may be detrimental and/or inefficient for a particular X-ray imaging procedure. For example, depending on the attenuation properties of the material being imaged, a particular dose, or quantity, of X-rays at a particular wavelength may be desired for generating the desired image data. Because a conventional X-ray tube typically emits X-rays not only at the desired wavelength but also at other wavelengths, conventional X-ray tubes may inadvertently increase the X-ray dosage received by the subject.

For example, some medical X-ray imaging procedures, such as angiography, employ a contrast agent, which is substantially opaque to X-rays of a given wavelength. The contrast agent is introduced into a particular artery or vein and images are captured which reveal the shape of the artery or the vein and which can help to diagnose an obstruction, blockage, or narrowing. Because the contrast agent is maximally opaque within narrow range of X-ray wavelengths, it is only necessary to employ X-rays within this range to achieve a good contrast to noise ratio (CNR), i.e., high quality image. A conventional X-ray tube however, emits X-rays not only in the desired narrow range but also at other wavelengths outside the narrow range, thereby subjecting the subject to a higher dose of X-rays than is necessary to obtain the desired image data. Likewise, other imaging techniques, both medical and non-medical, typically rely primarily on X-rays within a narrow range of wavelengths which interact suitably with the material of interest, such as bone, metal, etc. X-rays outside the narrow range of interest add little to the image quality.

Currently, selection of a suitable X-ray generation technique (such as the power of the electron beam and/or the composition of the target material) and filtration of the resulting broad spectrum of X-rays are used to control the wavelengths of X-rays generated and reaching the subject. These techniques, however, increase the size and weight of the X-ray source and are relatively expensive to implement. Furthermore, existing techniques for controlling X-ray spectral characteristics may be difficult to adjust to generate different X-ray spectra or particular, X-ray wavelengths.

Thus there exist a need for a method and system to easily generate X-rays having a narrow range of wavelengths. In particular, there is a need for a method and system for generating monochromatic X-rays having substantially the same wavelength.

BRIEF DESCRIPTION

In accordance with one embodiment, the present technique provides an X-ray source. The X-ray source includes an electron source configured to generate an electron beam. The X-ray source also includes an ultra-violet photon source configured to generate one or more mono-energetic streams of ultra-violet photons. The X-ray source further includes an interaction region configured to facilitate interaction of the electron beam and the one or more mono-energetic streams of ultra-violet photons to generate X-rays having a substantially monochromatic or multimodal distribution.

In accordance with one aspect of the present technique, a method of generating a monochromatic X-ray is provided. The method includes directing an electron beam towards an interaction region. The method also includes directing a one or more mono-energetic stream of ultra-violet photons towards the interaction region. The method further includes interacting the electron beam and the one or more mono-energetic stream of ultraviolet photons to generate a stream of substantially monochromatic or multimodal distribution X-rays.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally directed towards generating monochromatic X-rays, which may be used to generate images for medical and non-medical applications. As will be appreciated by those of ordinary skill in the art, the present techniques may be applied in various medical and non-medical applications, such as patient evaluation and passenger and/or baggage screening, to provide useful three-dimensional data and context. To facilitate explanation of the present techniques, however, a medical implementation will be generally discussed herein, though it is to be understood that non-medical implementations are also within the scope of the present techniques.

Figure 1:
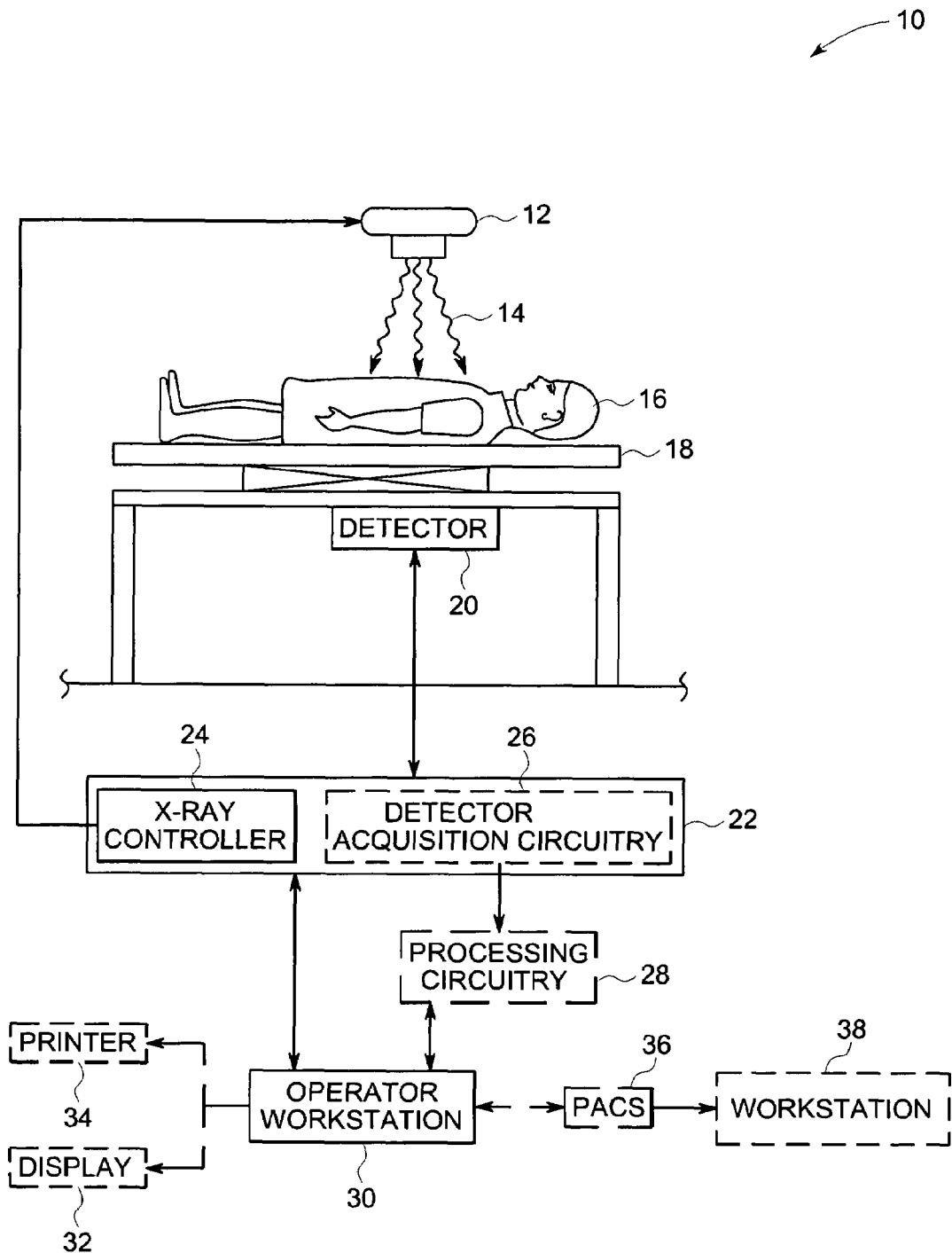
FIG. 1 is a diagrammatic representation of an X-ray imaging system, in accordance with an exemplary embodiment of present technique.

Turning now to the drawings, and referring first to FIG. 1, an exemplary embodiment of an X-ray imaging system 10 for use in accordance with the present technique is illustrated diagrammatically. As depicted, the X-ray imaging system 10 includes an X-ray source 12. In the present embodiment, the X-ray source 12 is configured to generate X-rays, which are generally monochromatic, though more than one monochromatic peak or wavelength may be present in the X-ray spectrum in some multi-modal embodiments. As used herein, the term "monochromatic" should be understood to mean a spectrum being primarily or substantially, though not necessarily exclusively, one wavelength. Such a monochromatic distribution, in practice, may consist of a primary, high, narrow peak centered about the desired wavelength. As noted above, in the present discussion, some embodiments are contemplated in which more than one such monochromatic distribution may be present, i.e., a "multi-modal" distribution. In such embodiments, however, it is still contemplated that each peak within the distribution is substantially monochromatic relative to the other non-peak, i.e., non-monochromatic, regions in the spectrum.

The X-ray source 12 is configured to emit X-ray beams 14 toward a patient 16 situated within an imaging volume that encompasses a specific region of interest in the patient 16. The X-ray imaging system 10 further includes a patient positioning system 18, which may position the patient 16 relative to the X-ray source 12 for imaging. The X-ray source 12 and or the patient positioning system 18 may be movable in one, two or three dimensions to different locations, either manually or by automated system, to allow image data acquisition at different view angles or of different regions of interest.

The X-ray imaging system 10 also includes detection circuitry to detect the X-ray beams 14, such as an X-ray detector 20. The X-ray detector 20 is generally situated across the imaging volume from the X-ray source 12 such that the region of interest of the patient 16 is disposed between the source 12 and detector 20. The X-ray detector 20 may be configured to generate an image in response to the incident X-rays on a film medium or to generate signals in response to the incident X-rays which may be acquired and digitally processed to generate an image. Accordingly, the X-ray detector 20 may include a housing for X-ray films along with such film or may instead comprise a digital detector assembly, including components such as a scintillator and photodiode array, for generating electrical signals in response to incident X-rays. Further, the X-ray detector 20 may be fixed into a stationary position or may be configured to move in coordination with or independent from the X-ray source 12.

In one embodiment, the X-ray imaging system 10 may include a system controller 22 to control the operation of the X-ray source 12 and/or the detector 20. In particular, in one embodiment the system controller 22 controls the activation and operation, including collimation and timing, of the X-ray source 12 via an X-ray controller 24. Similarly, in one embodiment the system controller 22 controls the operation and readout of the information from the X-ray detector 20 through detector acquisition circuitry 26. For example, in a digital implementation the detector acquisition circuitry 26 provides digital signals generated in response to the X-ray beams 14 to other components, such as processing circuitry 28.

In a digital implementation, the processing circuitry 28 is typically utilized to process and reconstruct the data from the detector acquisition circuitry 26 to generate one or more images for display. The processing circuitry 28 may include memory circuitry (not shown) to store the data before and/or after processing. The memory circuitry may also store processing parameters and/or computer programs that are utilized to process the signals associated with the images.

The processing circuitry 28 may be connected to other equipment, such as an operator workstation 30, a display 32, and a printer 34, to interact with an operator. For instance, the images generated by the processing circuitry 28 may be sent to the operator workstation 30 to be presented to an operator on the display 32. The processing circuitry 28 may also be configured to receive commands or processing parameters related to the processing or images or image data from the operator utilizing the operator workstation 30. The commands may be provided via input devices, such as a keyboard, a mouse, and other user interaction devices (not shown), which are part of the operator workstation 30. The operator workstation 30 may also be connected to the system controller 22 to allow the operator to provide commands and scanning parameters related to the operation of the X-ray source 12, via the X-ray controller 24, and/or of the detector acquisition circuitry 26. Hence, an operator may control the operation of different parts of the X-ray imaging system 10 via the operator workstation 30.

In addition, the operator workstation 30 may also be connected to other systems and/or components. For instance, the operator workstation 30 may be coupled to a picture archiving and communication systems (PACS) 36. The PACS 36 may be utilized to archive the captured X-ray images. Accordingly, the operator workstation 30 may access images or data accessible via the PACS 36 for processing by the processing circuitry 28, for displaying on the display 32, or for printing on the printer 34. Also, the PACS 36 may be coupled to a remote workstation 38 to provide remote access to the X-ray images.

Figure 2:
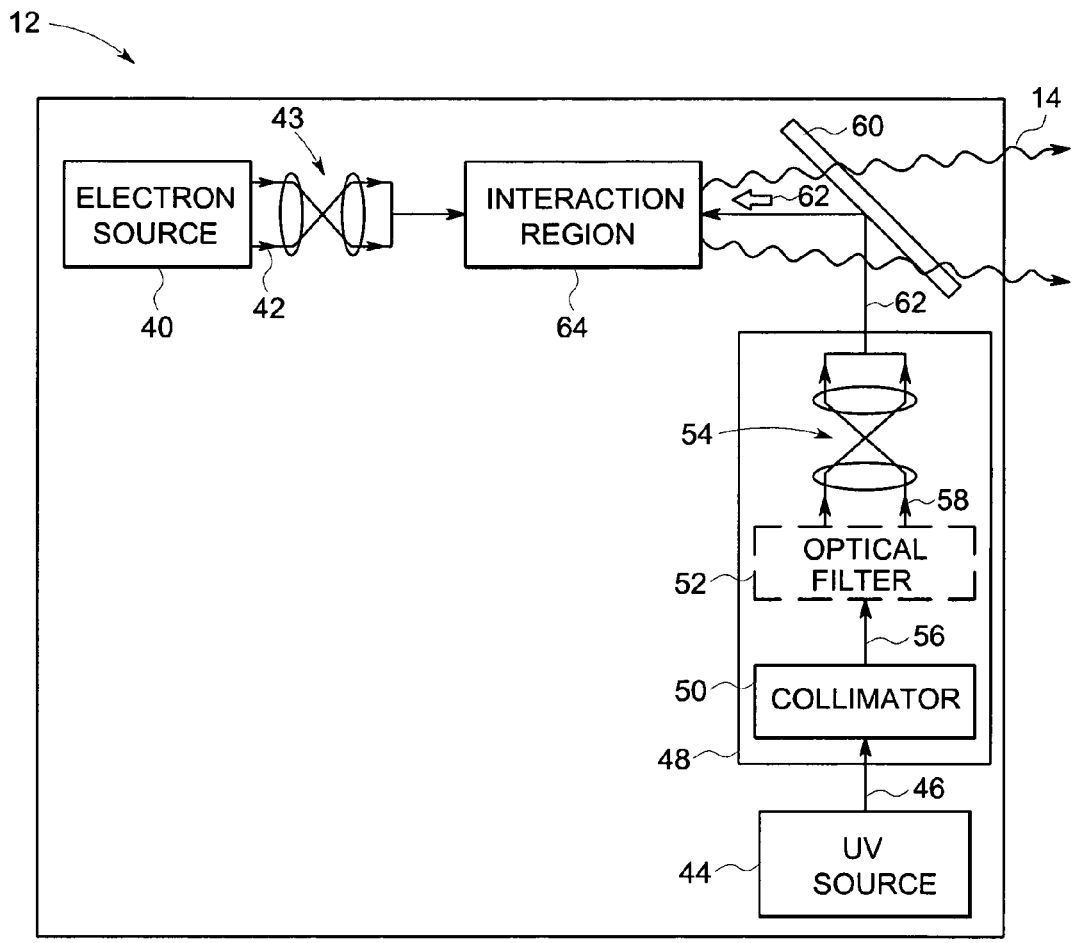
FIG. 2 is a diagrammatic representation of an X-ray source configured to generate monochromatic X-rays, in accordance with an exemplary embodiment of present technique.

Referring now to FIG. 2, a diagrammatic representation of an X-ray source 12 configured to generate monochromatic X-rays in accordance with an exemplary embodiment of present technique is provided. The X-ray source 12 includes an electron source 40. In one embodiment, the electron source 40 is a compact electron source, such as a source with comparable weight and size to a standard X-ray tube capable of being mounted on a C-arm, CT gantry or other standard X-ray tube positioning device. An example of such a compact electron source is a betatron. In other embodiments, the electron source 40 includes a linear accelerator, cyclotron, synchrotron or other electron storage ring or accelerator. The electron source 40 generates a high current electron beam 42 on the order of 1 to 20 million-electron-volts (MeV).

The X-ray source 12 also includes an ultra-violet (UV) source 44 of UV photons 46. For example, in one embodiment, the UV photon source 44 may be a high intensity lamp or a plasma source. As will be appreciated by those skilled in that art that the UV photon source may include any source that is capable of producing one or more mono-energetic streams of ultra-violet photons. In an embodiment in which the UV photons 46 are not generally monochromatic or otherwise encompass a broad UV spectrum, the X-ray source 12 includes a filter 48 having a collimator 50, optical filter 52 and a focusing optics 54. The filter 48 is utilized to transmit UV photon 46 of a desired wavelength and to block UV photons not at the desired wavelength. In one embodiment, the UV photons are generated or filtered to be monochromatic, typically within a frequency region or portion of UV spectrum in a multi electron-volt (eV) range of 5 to 30 eV. For example, the filter 48 may be used to select the 13.6 eV line of hydrogen when using hydrogen based arc lamp as the UV source 44.

In the depicted embodiment, the filter 48 includes a collimator 50, which directs the UV photons 46 in a desired direction and/or shapes the beam of UV photons. The collimated UV photons 56 then travel through an optical filter 52, which filters the UV photons 56 according to wavelengths. The filtered substantially monochromatic UV photons 58 then travel through focusing optics 54. In one embodiment, the focusing optics 54 is made of UV transparent materials and/or polished metals. In certain embodiments, lenses having selective transmission of UV wavelengths are used to make the collimator and/or focusing optics and hence are configured to function as filters. In such embodiments, the optical filter 52 may not be used. Furthermore, in embodiments in which the UV photon source 44 is disposed away from the desired X-ray path, a UV reflector 60 may be utilized to direct the monochromatic UV photons 62 towards an interaction region 64. The electron beam travels through a focusing optics 43 towards the interaction region 64. In the interaction region 64, the monochromatic UV photons 62 and electron beam 42 interact to generate monochromatic X-rays 14. In particular, as discussed herein, the electron beam 42 and the monochromatic UV photons 62 each enter the interaction region 64 such that in-line reflections generate a cone beam of substantially monochromatic X-rays 14 having full energy via Compton backscatter effect. The substantially monochromatic X-rays 14 generated in this manner have a high, narrow peak generally centered about the desired frequency. Alternatively, more than one set of monochromatic X-rays, i.e., a multimodal distribution, may be generated in which each peak corresponds to a generally monochromatic region of the X-ray distribution. Such a multi-modal distribution may be generated by using a multi-modal frequency distribution of UV photons 46 such that each peak of the UV photon distribution corresponds to peak of the X-ray distribution. In this way, an X-ray distribution having one or many substantially monochromatic X-ray peaks may be generated.

Figure 3:
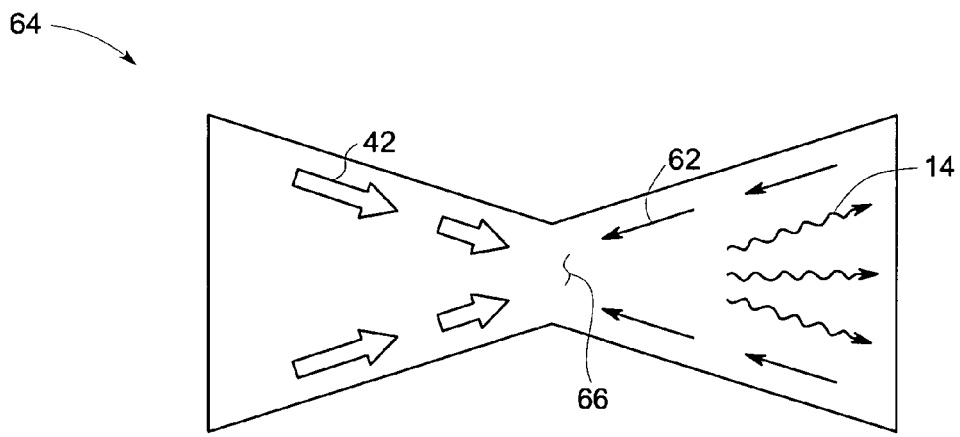
FIG. 3 is a diagrammatic representation of an interaction region of the X-ray source of FIG. 2.
Figure 4:
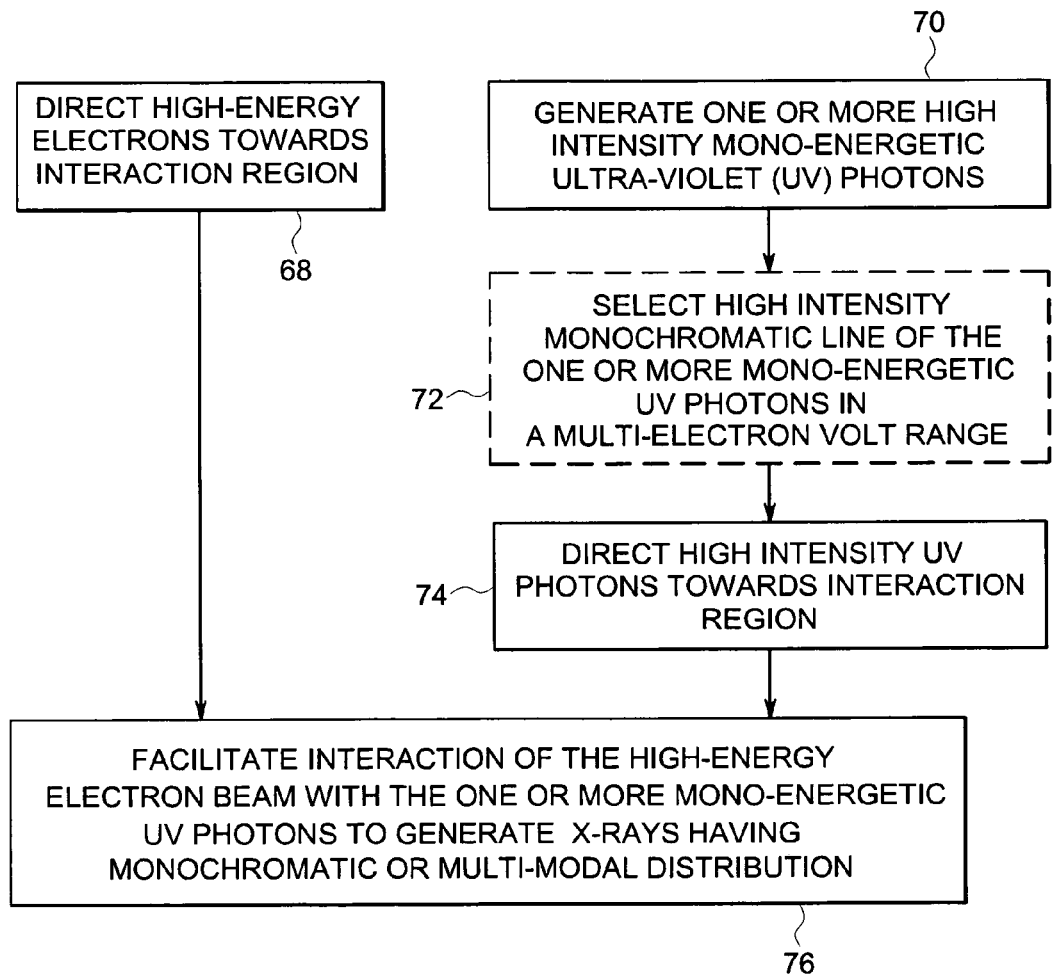
FIG. 4 is a flowchart illustrating an exemplary process for generating monochromatic X-rays, in accordance with aspects of present technique.

Keeping FIG. 2 in mind, FIG. 3 is a diagrammatic representation of the interaction region 64 of the X-ray source 12, in accordance with an exemplary embodiment of present technique. As described above, the interaction region 64 facilitates the interaction of the electron beam 42 and the monochromatic UV photons 62. In the depicted embodiment, the interaction region 64 has a circular or elliptical cross-section and a generally hourglass shape, which facilitates generation of a stream of monochromatic X-rays 14 in a fan or cone shape. In the cone shaped region UV photons are focused toward a region. The electron beam is also focused towards the same region, allowing for the incoming electrons to interact with the incoming UV photons in a head on arrangement. This allows for the cone beam to be uniform across its extent. The size and shape of the narrow central region 66 determine the size and shape of the fan or cone shape of the monochromatic X-rays 14.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An X-ray source, comprising:
   an electron source configured to generate an electron beam;
   an ultra-violet photon source configured to generate one or more mono-energetic streams of ultra-violet photons; and
   an interaction region configured to facilitate interaction of the electron beam and the one or more mono-energetic streams of ultra-violet photons to generate X-rays having a substantially monochromatic or multimodal distribution.

2. The X-ray source of claim 1, wherein the electron source is a betatron, cyclotron, synchrotron storage ring or a linear electron accelerator.

3. The X-ray source of claim 1, wherein the electron source is a compact electron source.

4. The X-ray source of claim 1, wherein the ultra-violet photon source comprises a high intensity lamp or a plasma source.

5. The X-ray source of claim 1, wherein the ultra-violet photon source is disposed away from a path of the stream of substantially monochromatic or multimodal distribution X-rays.

6. The X-ray source of claim 1, wherein the ultra-violet photon source comprises a filter configured to select a substantially monochromatic line of an ultra-violet radiation spectrum in a multi-electron volt range.

7. The X-ray source of claim 1, further comprising an ultra-violet reflector configured to direct the one or more mono-energetic stream of ultra-violet photons towards the interaction region.

8. The X-ray source of claim 1, wherein the interaction region is configured to generate a cone beam of X-rays.

9. The X-ray source of claim 1, wherein the interaction region is configured to generate the stream of substantially monochromatic or multimodal distribution X-rays in a cone-shape by simultaneously focusing the electron beam and UV photon beam on a region in space.

10. The X-ray source of claim 1, wherein the interaction region comprises a narrow circular or elliptical cross-section.

11. The X-ray source of claim 1, wherein a cross-section of the interaction region is configured to modify a shape of the stream of substantially monochromatic or multimodal distribution X-rays.

12. A method of generating X-rays having a substantially monochromatic or multimodal distribution, the method comprising the steps of:
   directing an electron beam towards an interaction region;
   directing a one or more mono-energetic stream of ultra-violet photons towards the interaction region; and
   interacting the electron beam and the one or more mono-energetic stream of ultraviolet photons to generate a stream of substantially monochromatic or multimodal distribution X-rays.

13. The method of claim 12, further comprising generating the stream of substantially monochromatic or multimodal distribution X-rays in a cone-shape.

14. The method of claim 12, further comprising selecting a substantially monochromatic line of an ultra-violet radiation spectrum in a multi-electron volt range.

15. The method of claim 12, further comprising directing the one or more mono-energetic stream of ultra-violet photons towards the interaction region.

16. A method of manufacturing X-rays having a substantially monochromatic or multimodal distribution, the method comprising the steps of:
   providing an electron beam source configured to generate an electron beam;
   providing an ultra-violet photon source configured to produce a stream of ultra-violet photons; and
   providing an interaction region configured for the interaction of the electron beam and the stream of ultraviolet photons by simultaneously focusing the electron beam and UV photon beam on a region in space.

17. The method of claim 16, comprising providing the ultra-violet photon source away from a path of a stream of substantially monochromatic X-rays.

18. The method of claim 16, further comprising displacing an ultra-violet reflector.

19. The method of claim 16, further comprising providing a filter in the ultra-violet photon source to select a substantially monochromatic line of an ultra-violet radiation spectrum in a multi-electron volt range.

20. An X-ray imaging system comprising:
   an X-ray source comprising:
      an electron source configured to generate an electron beam;
      an ultra-violet photon source configured to generate a stream of ultra-violet photons; and
      an interaction region configured to facilitate interaction of the electron beam and the stream of ultra-violet photons to generate a stream of substantially monochromatic X-rays;
   an X-ray detector configured to generate a plurality of signals in response to the emitted substantially monochromatic X-rays;
   acquisition circuitry configured to acquire the plurality of signals; and
   image-processing circuitry configured to generate one or more images based on the plurality of signals.

21. The X-ray imaging system of claim 20, wherein the electron source is configured to generate a high-energy accelerated electron beam.

22. The X-ray source of claim 20, wherein the ultra-violet photon source comprises a filter configured to select a substantially monochromatic line of an ultra-violet radiation spectrum in a multi-electron volt range.

* * * * *